US006793660B2

(12) United States Patent  
Kerr et al.

(10) Patent No.: US 6,793,660 B2
(45) Date of Patent: Sep. 21, 2004

(54) THREADED SYRINGE FOR DELIVERY OF A BONE SUBSTITUTE MATERIAL

(75) Inventors: Sean H. Kerr, Oreland, PA (US); Mark T. Fulmer, San Jose, CA (US)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/932,313

(22) Filed: Aug. 20, 2001

(65) Prior Publication Data

US 2003/0036762 A1 Feb. 20, 2003

(51) Int. Cl.⁷ ............................................. A61B 17/56
(52) U.S. Cl. ........................... 606/93; 606/94; 606/92
(58) Field of Search ................... 606/91–94; 604/211

(56) References Cited

U.S. PATENT DOCUMENTS

| 938,544 A | 11/1909 | Ball | |
|---|---|---|---|
| 2,130,305 A | 9/1938 | Lewis | 128/260 |
| 2,283,915 A | 5/1942 | Cole | 128/218 |
| 2,771,217 A | 11/1956 | Brown et al. | 222/43 |
| 2,853,070 A | 9/1958 | Julliard | 128/218 |
| 3,281,023 A | 10/1966 | Bruck et al. | 222/390 |
| 3,343,539 A | 9/1967 | Moorhouse | 128/234 |
| 3,353,718 A | 11/1967 | McLay | 222/158 |
| 3,384,274 A | 5/1968 | Lundvall | 222/383 |
| 4,184,490 A | 1/1980 | Jacklich | 128/236 |
| 4,189,065 A | 2/1980 | Herold | 222/46 |
| 4,312,343 A | 1/1982 | LeVeen et al. | 128/218 |
| 4,338,925 A | 7/1982 | Miller | 128/92 E |
| 4,346,708 A | 8/1982 | LeVeen et al. | 128/236 |
| 4,367,739 A | 1/1983 | LeVeen et al. | 128/236 |
| 4,444,560 A | 4/1984 | Jacklich | 604/224 |
| 4,498,904 A | 2/1985 | Turner et al. | 604/211 |
| 4,568,335 A | 2/1986 | Updike et al. | 604/211 |
| 4,576,152 A | 3/1986 | Müller et al. | 128/92 R |
| 4,592,745 A | 6/1986 | Rex et al. | 604/211 |
| 4,655,749 A | 4/1987 | Fischione | 694/98 |
| 4,671,263 A | 6/1987 | Draenert | 128/92 |
| 4,710,172 A | 12/1987 | Jacklich et al. | 604/118 |
| 4,710,179 A | 12/1987 | Haber et al. | 604/211 |
| 4,732,302 A | 3/1988 | Mühlbauer | 222/390 |
| 4,743,230 A | 5/1988 | Nordquest | 604/97 |
| 4,744,955 A | 5/1988 | Shapiro | 422/100 |
| 4,810,249 A | * 3/1989 | Haber et al. | 604/210 |
| 4,820,287 A | 4/1989 | Leonard | 604/209 |
| 4,852,768 A | 8/1989 | Bartsch | 222/46 |
| 4,863,072 A | 9/1989 | Perler | 222/390 |
| 4,925,449 A | 5/1990 | Saez et al. | 604/227 |
| 4,929,238 A | 5/1990 | Baum | 604/208 |
| 4,966,601 A | 10/1990 | Draenert | 606/92 |
| 4,973,318 A | 11/1990 | Holm et al. | 604/208 |
| 4,994,065 A | 2/1991 | Gibbs et al. | 606/92 |
| 5,057,078 A | 10/1991 | Foote et al. | 604/99 |
| 5,071,040 A | 12/1991 | Laptewicz, Jr. | 222/235 |
| 5,078,690 A | 1/1992 | Ryan | 604/187 |
| 5,137,514 A | 8/1992 | Ryan | 604/99 |
| 5,141,495 A | 8/1992 | Olovson | 604/110 |

(List continued on next page.)

FOREIGN PATENT DOCUMENTS

| DE | 344167 | 11/1921 |
|---|---|---|
| WO | WO 99/18865 | 4/1999 |
| WO | WO 99/18866 | 4/1999 |
| WO | WO 99/18894 | 4/1999 |
| WO | WO 99/49819 | 10/1999 |

*Primary Examiner*—Cary E. O'Connor
*Assistant Examiner*—Candice C. Melson
(74) *Attorney, Agent, or Firm*—Jones Day (57) ABSTRACT

The invention relates to a syringe for delivery of a bone substitute material. The syringe includes a barrel for holding the material, a plunger receivable within the barrel and having a threaded portion, and an engagement member including a threaded throughbore positioned coaxial with the barrel. The threaded portion of the plunger is movable through the threaded throughbore barrel by pushing the plunger in the axial direction, and by rotating the plunger. The invention also relates to a method of expelling material from a syringe.

53 Claims, 11 Drawing Sheets

U.S. PATENT DOCUMENTS

| | | | |
|---|---|---|---|
| 5,160,327 A | 11/1992 | Stines | 604/224 |
| 5,183,466 A | 2/1993 | Movern | 604/110 |
| 5,284,480 A | 2/1994 | Porter et al. | 604/97 |
| 5,290,260 A | 3/1994 | Stines | 604/224 |
| 5,300,041 A | 4/1994 | Haber et al. | 604/207 |
| 5,339,830 A | 8/1994 | Blake, III | 128/771 |
| 5,472,424 A | 12/1995 | Lampropoulos et al. | 604/99 |
| 5,591,136 A | 1/1997 | Gabriel | 604/211 |
| 5,599,314 A | 2/1997 | Neill | 604/207 |
| 5,603,701 A | 2/1997 | Fischer | 604/211 |
| 5,618,273 A * | 4/1997 | Fischer | 604/211 |
| 5,638,997 A | 6/1997 | Hawkins et al. | 222/391 |
| 5,656,034 A | 8/1997 | Kochersperger et al. | 604/155 |
| 5,728,075 A | 3/1998 | Levander | 604/211 |
| 5,743,889 A | 4/1998 | Sams | 604/211 |
| 6,019,765 A * | 2/2000 | Thornhill et al. | 606/94 |
| 6,019,776 A | 2/2000 | Preissman et al. | 606/185 |
| 6,033,411 A | 3/2000 | Preissman | 606/99 |
| 6,383,190 B1 | 5/2002 | Preissman | 606/94 |
| 2002/0049448 A1 | 4/2002 | Sand et al. | 606/92 |
| 2002/0099384 A1 | 7/2002 | Scribner et al. | 606/92 |
| 2003/0032964 A1 | 2/2003 | Watkins et al. | 606/93 |

* cited by examiner

THREADED SYRINGE FOR DELIVERY OF A BONE SUBSTITUTE MATERIAL

FIELD OF THE INVENTION

The invention relates to a threaded syringe. More particularly, this invention relates to a syringe for use in the delivery of a bone substitute material.

BACKGROUND OF THE INVENTION

Injectable bone substitute materials are used for the repair and augmentation of orthopedic fractures and defects. Bone substitute materials can also be used in certain diagnostic or therapeutic procedures that require the formation of a cavity in a bone mass. This procedure can be used to treat any bone, for example, bone which due to osteoporosis, avascular necrosis, cancer, or trauma, is fractured or is prone to compression fracture or collapse. These conditions, if not successfully treated, can result in deformities, chronic complications, and an overall adverse impact upon the quality of life.

Furthermore, it is known that during some surgical operations, it is necessary to inject a relatively large quantity of bone substitute material at relatively low pressure and thereafter to inject a small quantity of material at relatively high pressure without applying substantially increased force. However, especially with highly viscous or solid, yet pliable cement compositions, it is often difficult with a standard push-type syringe to generate the pressure needed to express the material through the syringe outlet opening by exerting pressure on the syringe plunger in an axial direction. Another serious problem is that once sufficient pressure is applied to the plunger, it is difficult to precisely control the amount of material expelled through the outlet opening of the barrel, resulting in extraosseous (i.e., outside the bony cavity) flow.

Various types of devices have been used for delivering bone substitute material, such as bone cement. For example, injector guns having a trigger mechanism that includes a trigger in the form of a lever have been used. Also, standard push-type syringes comprising a barrel and a plunger may be used for such purposes.

A bone cement gun is described in U.S. Pat. No. 5,638,997 as having a trigger mechanism that has first and second mechanical advantages corresponding to the trigger stroke. The first mechanical advantage facilitates generating a high pressure in the U.S. Pat. No. 4,338,925, a trigger gun is disclosed that utilizes a trigger mechanism with a constant mechanical advantage.

Trigger guns, however, generally lack the improved tactile feedback available using a syringe apparatus. Such improved tactile feedback is important to notify the surgeon when there is an occlusion or other blockage which prevents the material from exiting the delivery device, or in the performance of sensitive procedures such as in repair of the vertebra.

One type of injector or syringe for injecting bone cement into surgically prepared bone cavities is described in European Patent B 1-006430. The bone cement injector consists of a piston and cylindrical tube to which a nozzle element having a nozzle tube of relatively narrow cross-section is attached. Such an injector is constructed so as to permit the mixing and extrusion of a pasty bone cement in a simple manner. In this regard, the nozzle tube is made as a two-part member of relatively narrow cross-section.

Another type of syringe for bone cement is described in U.S. Pat. No. 4,576,152. The injector is provided with an injection nozzle in the bottom of the cylinder tube for low pressure operation to deliver large quantities of bone cement. A nozzle element can be releasably attached to the cylinder tube for high pressure injection. The nozzle element is removed for low pressure injection and attached for high pressure injection.

SUMMARY OF THE INVENTION

The invention relates to a syringe for delivery of a bone substitute material. The syringe includes a barrel for holding the material, a plunger receivable within the barrel and having a threaded portion, and an engagement member including a threaded throughbore positioned coaxial with the barrel. The threaded portion of the plunger is movable through the threaded throughbore barrel by pushing the plunger in the axial direction, and by rotating the plunger.

The preferred engagement member has a C-shape and includes a slot extending radially therethrough. In addition, the preferred engagement member is expandable in the radial direction. In one embodiment, the cross-sectional area of the throughbore is variable. In another embodiment, the throughbore includes an inner surface that is in full contact with the plunger when the plunger moves therethrough.

In another preferred embodiment, the material exits the barrel under a first pressure when the plunger is pushed in the distal direction and the material exits the barrel under a second pressure when the plunger is advanced through rotation. Preferably, an audible noise is made as the threaded portion plunger moves past the engagement member when the plunger is pushed in the axial direction. Preferably, a predetermined amount of material is expelled from the barrel with each audible click. In addition, a predetermined amount of material is expelled from the barrel when the barrel is advanced with each rotation of the plunger.

Preferably, the syringe also includes a coupling member configured to receive a portion of a package containing material to facilitate the transfer of material from the package to the barrel. The preferred coupling member includes a funnel member to funnel the material into the barrel.

Preferably, the syringe also includes a finger grip coupled to the barrel at the proximal end and the engagement member is housed within the finger grip. In one embodiment, the finger grip comprises a pair of half shells. In the preferred embodiment, the engagement member is movable within the finger grip between a first position to allow the plunger to advance by pushing the plunger in the axial direction and a second position to allow the plunger to advance by rotating the plunger. The preferred engagement member includes an extension arm that contacts the inner wall of the finger grip when the engagement member is in the first position. Preferably, the engagement member engages a seat for preventing the engagement member from expanding when the engagement member is in the second position.

The invention also relates to a method of expelling material from a syringe having a barrel with an engagement member, and a plunger. A preferred method includes the step of moving the plunger within the barrel by pushing the plunger through the engagement member and moving the plunger within the barrel by rotating the plunger through the engagement member.

DETAILED DESCRIPTION OF THE PREFERRED EMBODIMENTS

Figure 1:
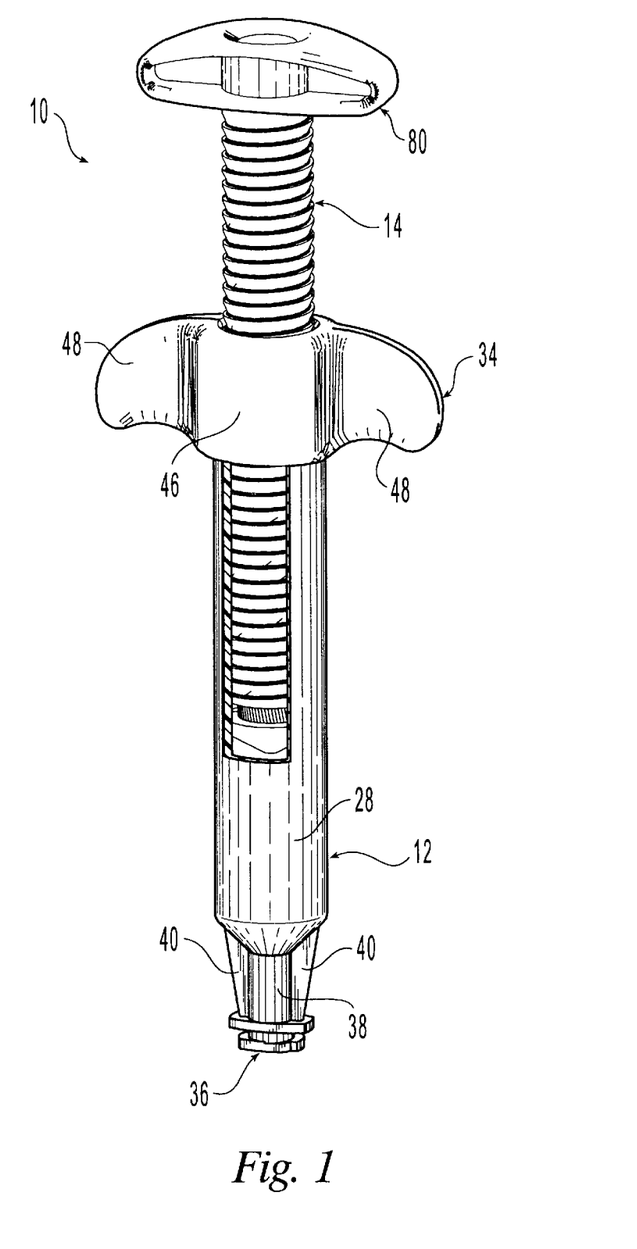
FIG. 1 is a perspective view of a syringe apparatus constructed according to the present invention.
Figure 2:
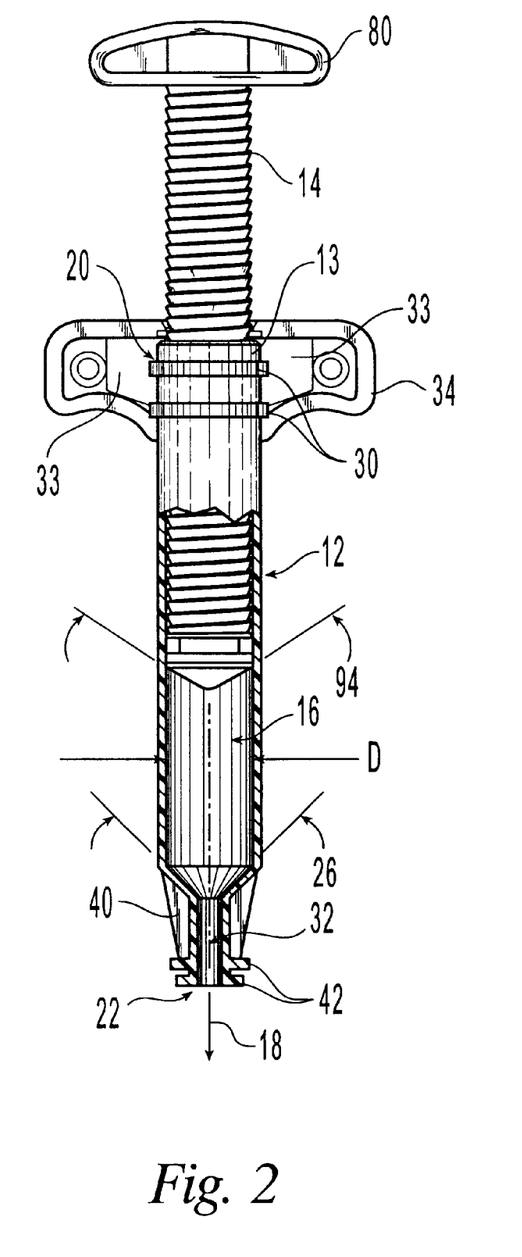
FIG. 2 is a front view of the syringe of FIG. 1 showing a cross-sectional view of the finger grip.

Referring generally to FIGS. 1 and 2, a first embodiment of a syringe 10 constructed according to the present invention comprises a cylindrical body or barrel 12, an engagement member 13, and a threaded plunger 14. The syringe is intended for use in the delivery of a medicament, preferably for the delivery of material that promotes recovery from injury or ailment of the bones. Some examples of suitable material applicable in the therapeutic treatment of bone include polymethylmethacrylate (PMMA), calcium phosphate cements, such as NORIAN Calcium Phosphate Bone Cement available from Norian Corporation of Cupertino, Calif., calcium sulphate cements, demineralized bone suspensions, or other bone filler material or bone substitutes. In the preferred embodiment, syringe 10 is intended to deliver relatively highly viscous or solid, yet pliable materials, or materials that have a relatively low liquid to solid ratio, such as a paste.

Barrel 12 includes a central channel or bore 16 extending along a longitudinal axis 18 of barrel 12 from a proximal end 20 to a distal end 22. The interior of bore 16 is substantially cylindrical and preferably has a diameter D of about 0.625 inches. An exit channel 32 is in fluid communication with bore 16 at the distal end of bore 16 and has a diameter smaller than that of bore 16 for expelling contents of barrel 12 therethrough when the syringe 10 is used. The interior wall of bore 16 is tapered at a reducer angle 26 at the distal end to transition to the smaller diameter exit channel 32. In the preferred embodiment, the reducer angle 26 is about 90 degrees included to facilitate the transfer of material out of bore 16 and into exit channel 32. Barrel 12 has a generally cylindrical outer surface 28 and preferably has at least one circular flange 30 at the proximal end 20 that extends radially beyond the outer surface 28. A pair of planar finger grip mounts 33 extend radially outward from and longitudinally beyond the proximal end 20 of barrel 12 for supporting a finger grip 34.

A needle attachment portion 36 is formed at the distal end 22 of syringe 10. Needle attachment portion 36 includes a central cylinder 38 that extends in the distal direction from the distal end of barrel 12 and defines the exit channel 32 on its interior. A pair of fins 40 extend from the distal end of barrel 12 to the distal end 22 of syringe 10. At least one flange 42 is positioned at the distal end of needle attachment portion 36 to facilitate the attachment of a needle or the like to the distal end 22 of syringe 10.

The finger grip 34 is coupled to the finger grip mounts 33 at proximal end 20 of syringe 10 and is configured to accommodate the fingers of the user when the syringe is used. In a preferred embodiment, finger grip 34 comprises a pair of half shells 44 fitted over mounts 33 and attached together in a mating relationship, such as by ultrasonic welding. Preferably, the distal portion of the finger grip 34 abuts a circular flange 30 so that when the syringe is used, any force exerted upon finger grip 34 in the proximal direction is transferred to the barrel 12 and vice versa. A portion of the interior of the finger grip 34 abuts or contacts the mounts 33 so that any rotational force transmitted to finger grip 34 is transferred to barrel 12 and vice versa. The exterior of finger grip 34 includes a central cylindrical portion 46 having a diameter slightly greater than that of barrel 12 and a pair of finger portions 48 oriented parallel to the longitudinal axis 18 of barrel 12. The interior of finger grip 34 is at least partially hollow and houses the engagement member 13 therein. In the preferred embodiment, engagement member 13 is free to expand in the radial direction and move in the axial direction within the interior of central cylindrical portion 46. In alternate embodiments, engagement member 13 can be housed in barrel 12, or be formed integral therewith.

Figure 3:
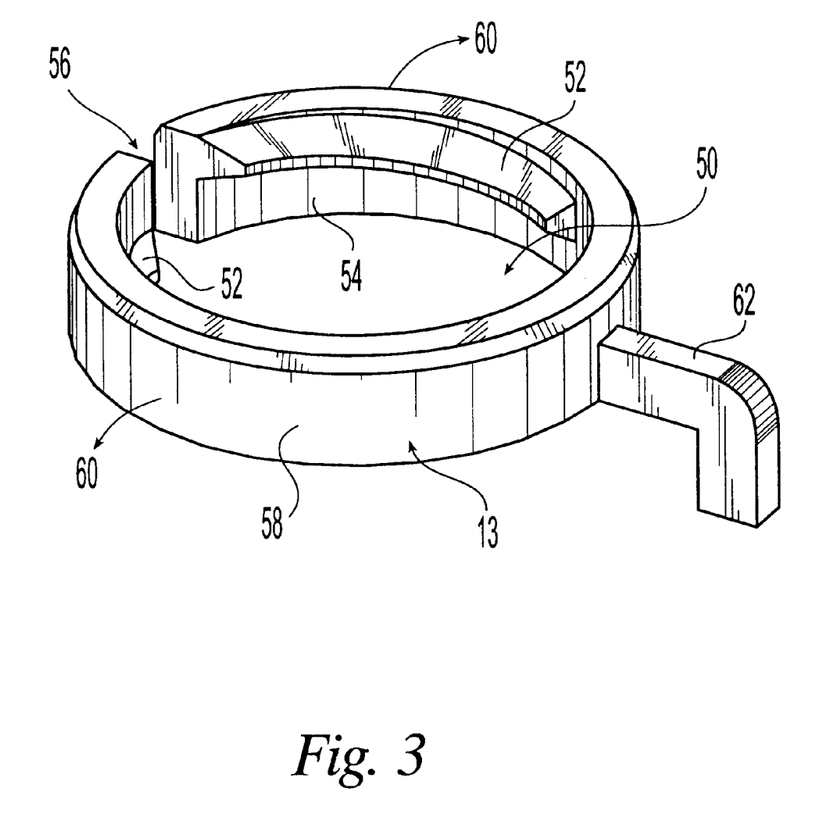
FIG. 3 is a perspective view of an engagement member of the syringe of FIG. 1.
Figure 11A:
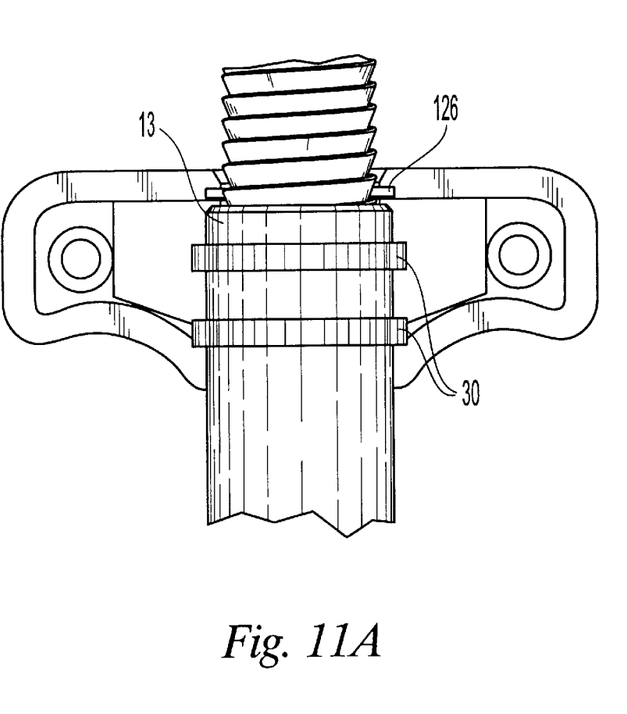
FIGS. 11A–B are partial cross-sectional views of the finger grip of FIG. 1 depicting the engagement member in first and second positions respectively.

Referring to FIGS. 2 and 3, the engagement member 13 is positioned adjacent proximal end 20 of barrel 12 and includes a threaded throughbore 50 having threads 52 on its inner surface 54. Threads 52 of engagement member 13 are complimentary to the threads of plunger 14. In the preferred embodiment, engagement member 13 has a C-shape with an outer diameter which generally corresponds to the diameter of circular flange 30 described above. A slot 56 extends radially from the throughbore 50 to the exterior surface 58 of the engagement member 13 to allow for engagement member 13 to expand in the radial direction, as shown by arrows 60 in FIG. 3. In the preferred embodiment, engagement member 13 and threaded throughbore 50 are situated within finger grip 34 such that they are in axial alignment with the central bore 16 of barrel 12. Slot 56 is aligned with and engages one of finger grip mounts 33 and a portion of the exterior surface 58 of engagement member 13 abuts the other finger grip mount 33. Engagement member 13 is movable in the axial direction within the interior of finger grip 34. Engagement member 13 is movable between a first position at the distal side of finger grip 34 where the engagement member abuts or contacts barrel 12, shown in FIG. 11A, and a second position at the proximal side of finger grip 34 where the engagement member abuts or contacts the interior wall of the finger grip, shown in FIG. 11B. The engagement member 13 is prevented from rotation by the slot 56 as it is engaged with finger grip mount 33. Engagement member 13 includes an extension arm 62 that contacts the interior wall of finger grip 34 when the engagement member is in the first position and provides a readily identifiable feature of the engagement member to assist in the proper assembly of syringe 10.

Figure 4:
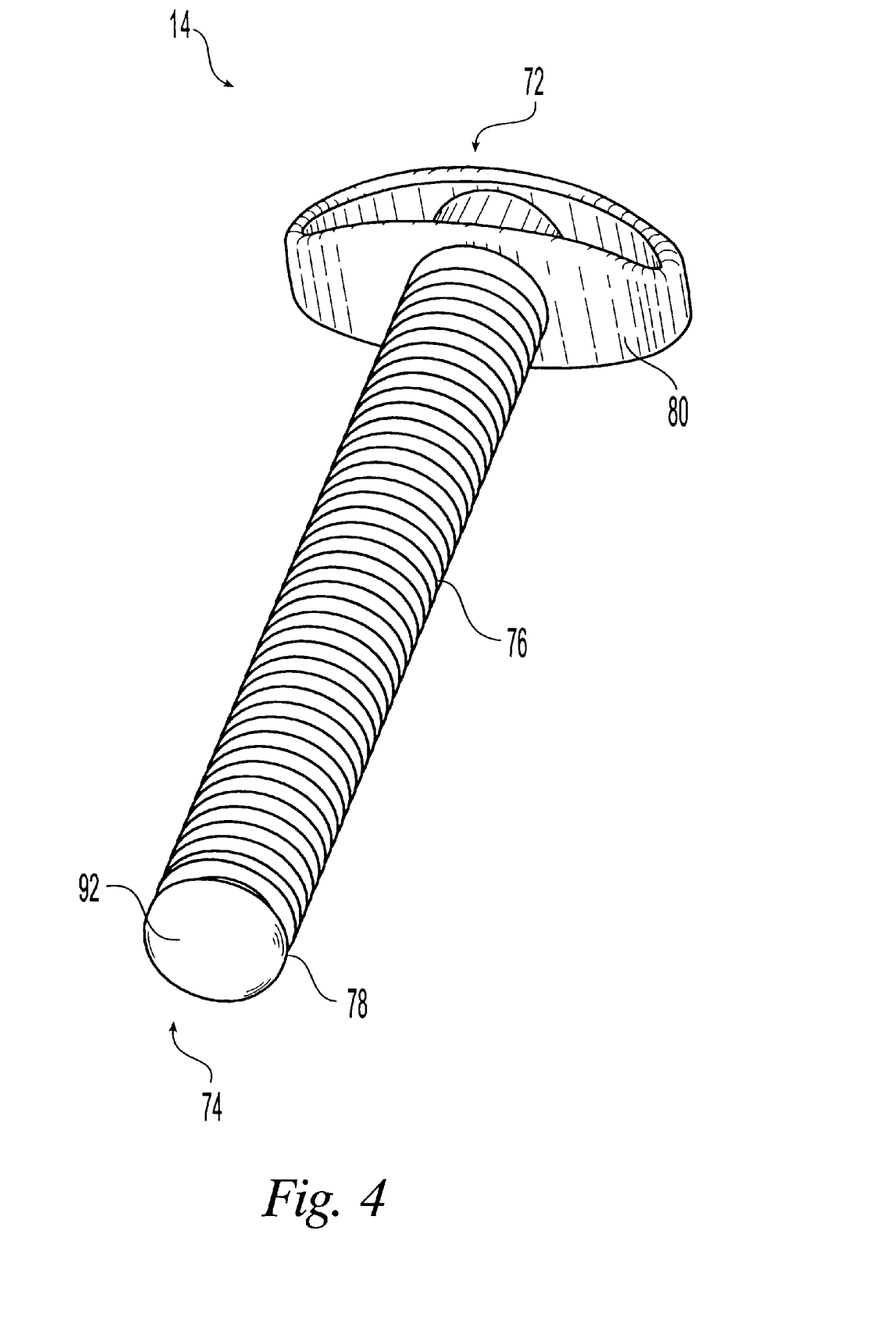
FIG. 4 is a perspective view of the threaded plunger of FIG. 1.
Figure 5:
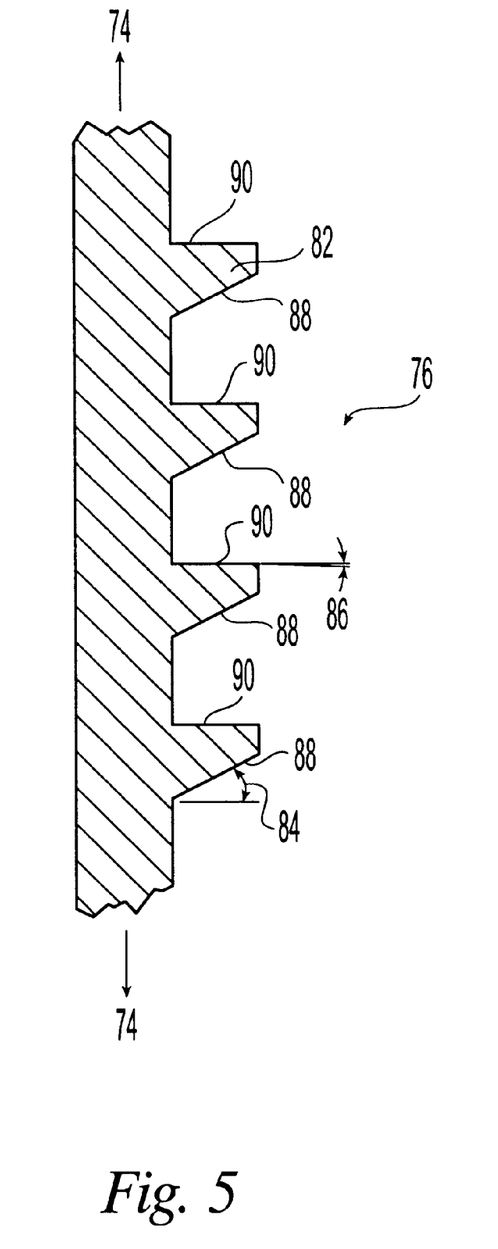
FIG. 5 is a partial, longitudinal, cross-sectional profile view of threads of the threaded plunger of FIG. 1.
Figure 6:
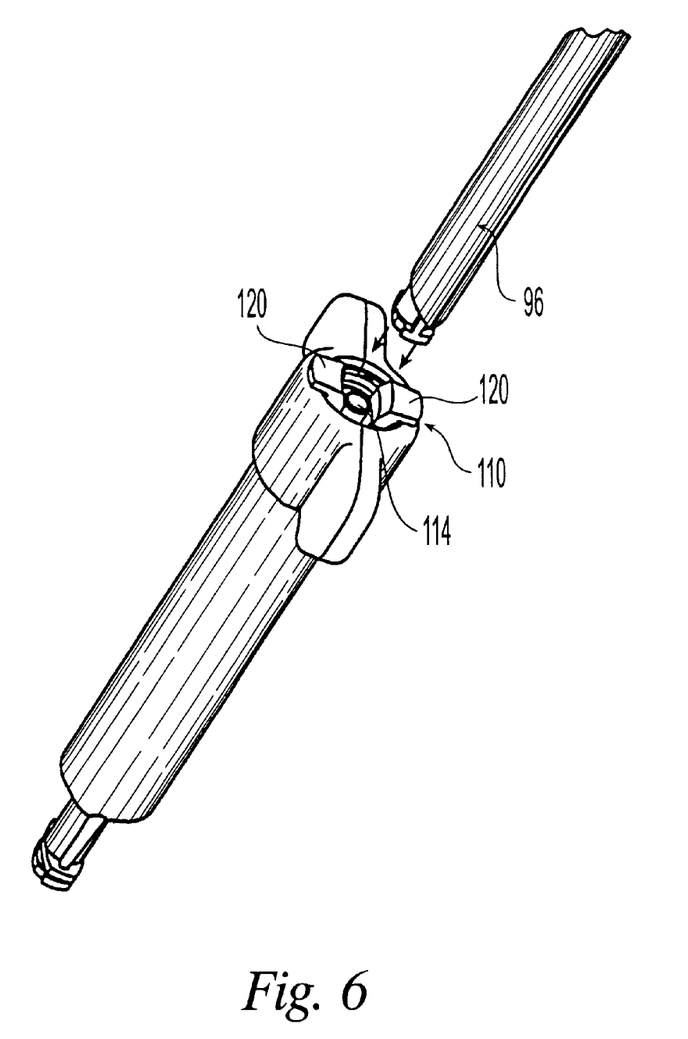
FIG. 6 is an exploded, perspective view depicting the attachment of a tube of material with the syringe of FIG. 1.

Referring to FIG. 4, plunger 14 has a proximal end 72, a distal end 74, a threaded stem 76, an unthreaded distal tip 78, and an integrally formed, handle shaped head 80. The external threads 82 of threaded stem 76 are complementary of, and configured to mate with, the internal threads 52 of engagement member 13. The outside diameter of the threads 82 of threaded stem 76 is approximately the same, yet is slightly smaller than, the internal diameter D of central bore 16 of barrel 12, such that threaded stem 76 will slide with close tolerance within central bore 16. In one preferred embodiment, the pitch of threads 82 of the threaded stem 76 is about 0.10 inches, or about ten threads per inch. Preferably the flank angles 84, 86 of threads 82 are not symmetrical. As can be seen in FIG. 5, leading flank surfaces 88 of respective threads 82 of threaded stem 76 each have a leading flank angle 84. In the preferred embodiment, leading flank angle is about 60 degrees, however, leading flank angle 84 preferably is between about 45 to about 75 degrees. Trailing flank surfaces 90 each have a trailing flank angle 86 of between about 0 to about 10 degrees, preferably 0 degrees. The preferred flank angles facilitate the delivery of material from syringe 10 in a push-type fashion and prevent plunger 14 from being pushed or forced in the proximal direction when in use. The aforedescribed thread profile clearly constitutes a departure and modification from that of an Acme thread profile. The reader is referred to Machinery's Handbook. Twenty-fourth Edition, Industrial Press Incorporated, New York, N.Y., for a more detailed description of the terms utilized herein to describe the threads and their constituent parts.

To prevent the material from flowing back up between the threads of threaded stem 76 as it is advanced into barrel 12, the outside diameter of unthreaded tip 78 is approximately the same, yet is slightly smaller than, the internal diameter of central bore 16, such that unthreaded tip 78 will slide with close tolerance within central bore 16. Unthreaded tip 78 also has an annular recess for receiving an o-ring of suitable size (not shown) so as to provide a more effective seal against the inner surface of central bore 16. The distal end 74 of unthreaded tip 78 has an angled tip surface 92, which facilitates expelling a maximum amount of material out of the syringe 10. In a preferred embodiment, the distal end of tip 78 has a plunger angle 94 of between about 95 and 145 degrees, more preferably between about 105 and 135 degrees, most preferably about 120 degrees. It has also been determined that it is desirable that plunger angle 94 does not equal the reducer angle 26. It is also preferable that the plunger angle 94 is greater than the reducer angle 26 so that a maximum amount of material can exit the syringe.

Plunger 14 can be axially pushed or rotated through engagement member 13 to advance within barrel 12. The plunger 14 is movable through the threaded throughbore 50 of engagement member 13 along the longitudinal axis 18 of barrel 12 by pushing the plunger in the axial direction. The plunger 14 can also be moved along the longitudinal axis of barrel 12 by rotating the plunger such that the threads 82 of threaded stem 76 of plunger 14 engage the threads 52 of threaded throughbore 50.

Referring to FIGS. 6–9, in a preferred embodiment a coupling member 110 can be attached to the proximal end 20 of barrel 12 to facilitate the insertion of material into barrel 12. Coupling member 110 is adapted to fit a package or tube 96 having a coupler 98 to facilitate the transfer of material held in tube 96 to the syringe.

Figure 7:
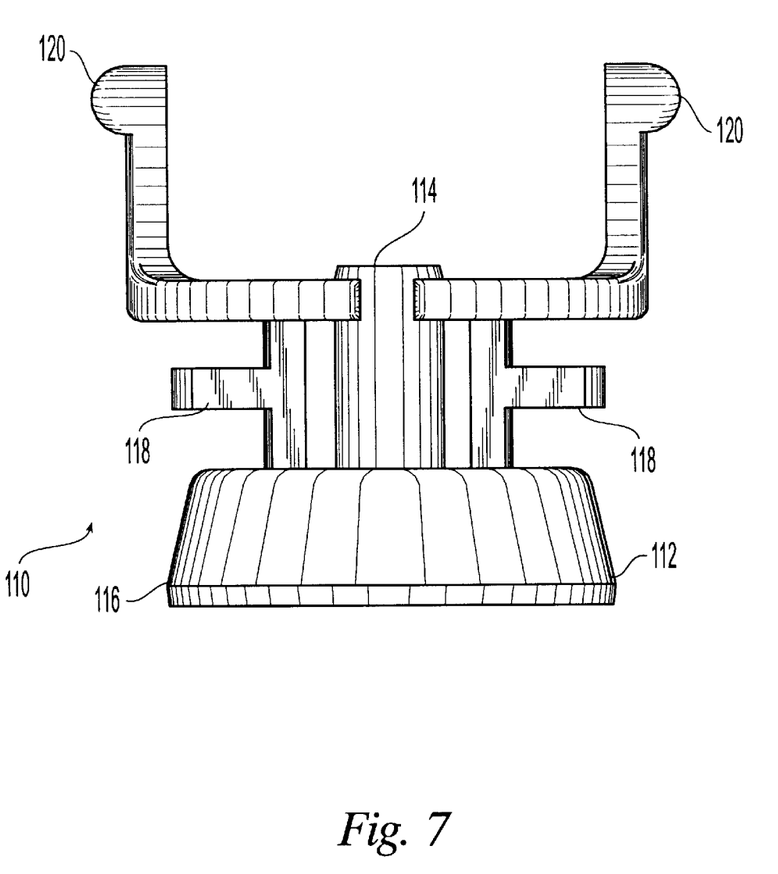
FIG. 7 is a perspective view of a coupling member of FIG. 6.
Figure 8:
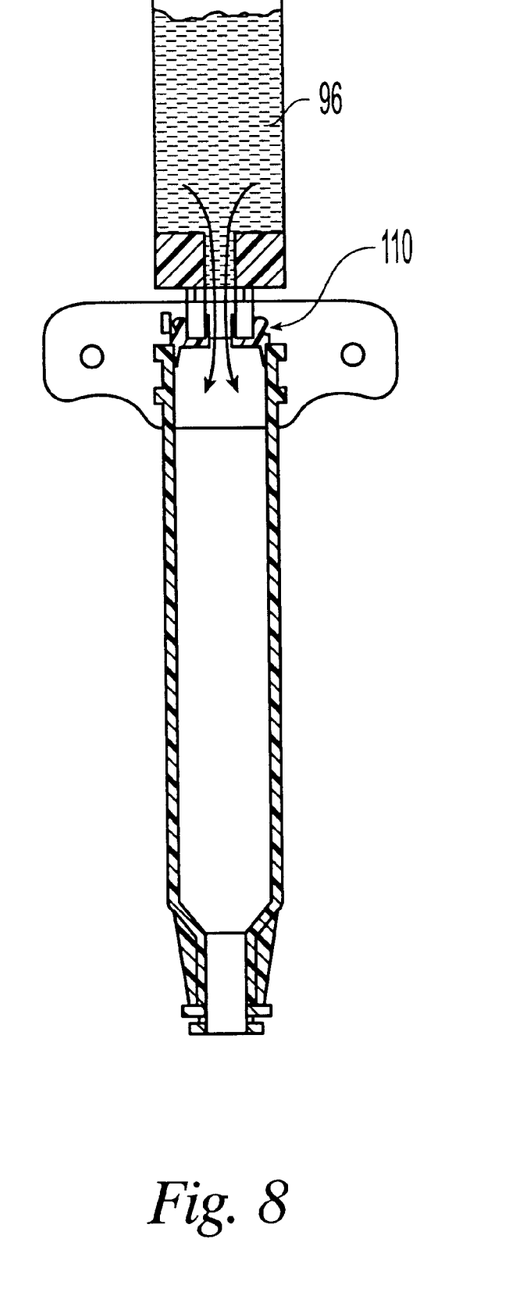
FIG. 8 is front, cross-sectional view depicting the transfer of material to the syringe of FIG. 1.
Figure 9:
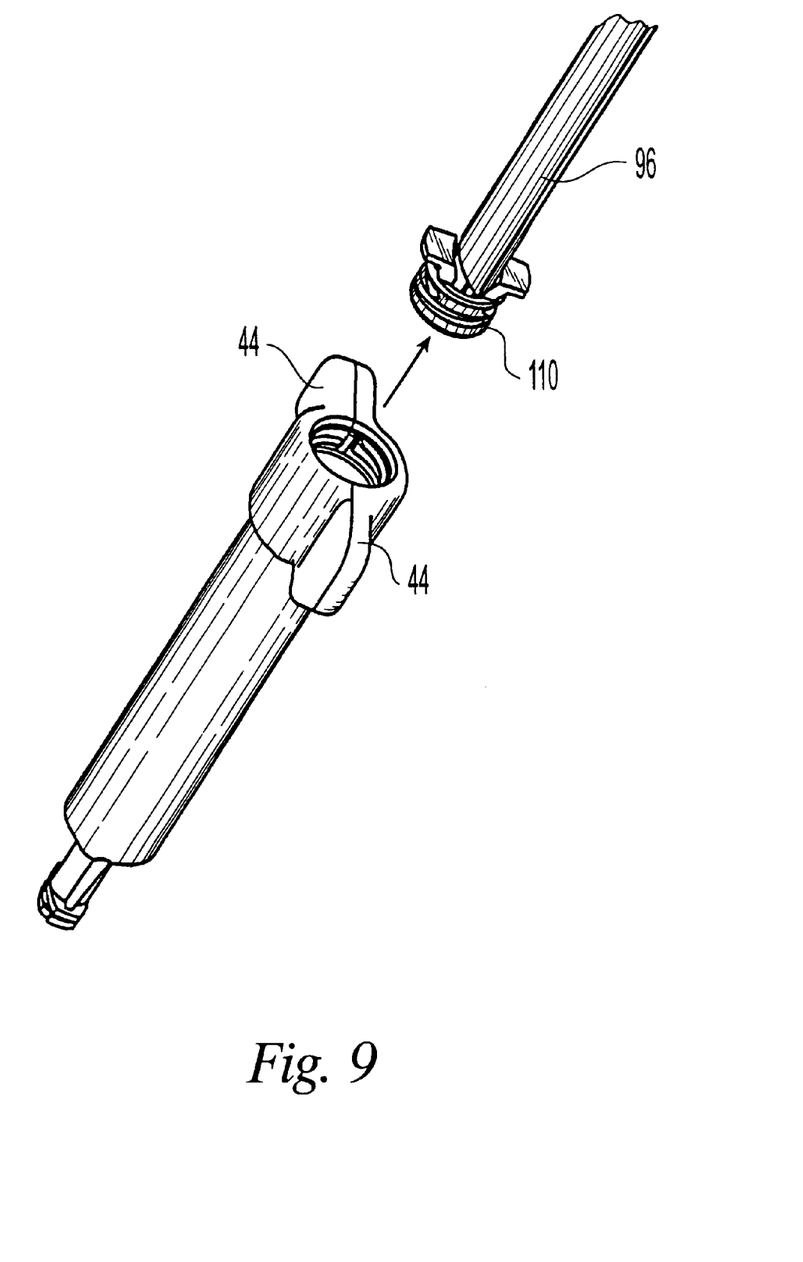
FIG. 9 is a perspective view of the tube of FIG. 6 as it is detached from the syringe of FIG. 1.

One preferred coupling member 110, shown in FIG. 7, includes an inverted central funnel member 112 having a relatively narrow cylindrical nose 114 extending 110 upward from a wider mouth portion 116 at its base. Thread engaging fingers 118 are spaced from mouth portion 116 and are configured to engage threads 52 of engagement member 13. A pair of release arms 120 extend radially outward from the top of nose 114 and facilitate the insertion and removal of coupling member 110 with respect to the proximal end 20 of barrel 12. As can be seen in FIG. 8, once coupling member 110 is inserted into the proximal end 20 of barrel 12, coupler 98 of tube 96 engages coupling member 110 and nose 114 extends into coupler 98. With tube 96 engaged with barrel 12, the material in tube 96 can be easily transferred therefrom, for instance by squeezing tube 96. As material enters barrel 12, inverted funnel 112 of coupling member 110 advantageously diverts the material through engagement member 13 and protects engagement member 13 from contacting the material during transfer. Maintaining the engagement member free from material is desirable to allow the engagement member to freely move during operation of the syringe. Referring to FIG. 9, once sufficient material has been transferred to barrel 12, the coupling member 110 and tube 96 can be easily removed form syringe 10 by accessing release arms 120 and disengaging fingers 118 from threads 52.

Figure 10:
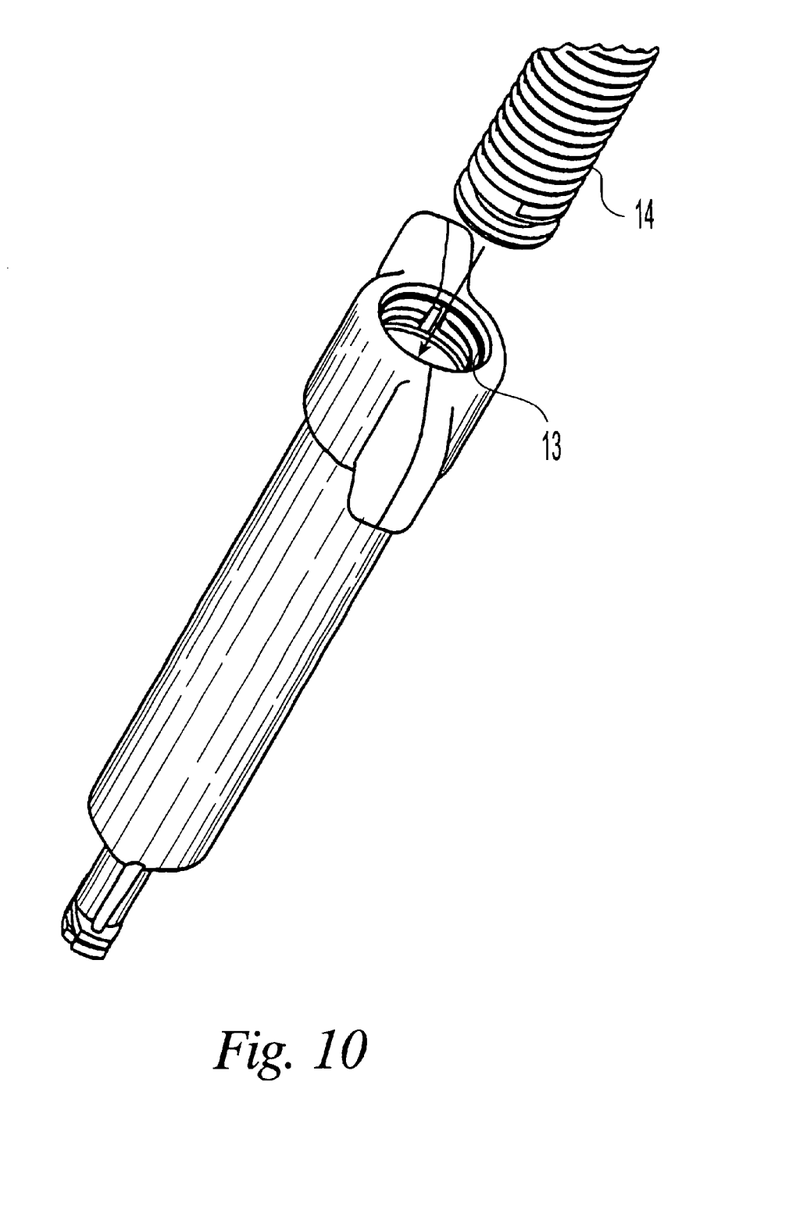
FIG. 10 is a perspective view showing the insertion of the plunger of FIG. 4 into the barrel of FIG. 1.

Referring now to FIG. 10, once the material is situated in barrel 12, plunger 14 is inserted into the proximal end 20 of barrel 12 through engagement member 13 and extends into the central bore 16 of barrel 12. The material can be expelled under both low and high pressure as desired. For example, a low pressure may be appropriate to expel a large amount of material while a high pressure may be appropriate for instances where the material must flow into a closed cavity, or penetration into cancellous bone is desired. In some embodiments between about 100 psi and about 500 psi must be generated to inject the treatment material at a sufficient rate. It is noted that it is desirable for the user to receive tactile feedback during the insertion of the material so that the material is delivered under optimum pressure depending on the procedure involved.

The material can be expelled under low pressure by pushing plunger 14 in an axial direction. As explained above, the flank angles 84, 86 of the threads 82 are not symmetrical, but rather have a lead surface 88 with a leading flank angle 84. As such, when the plunger is advanced or pushed in the axial direction, this leading flank angle 84 guides the engagement member 13 into an area within the finger grip 34 where it can resiliently expand in the radial direction, as shown by arrows 60 in FIG. 3. In this regard, the cross-sectional area of the throughbore 50 varies with the expansion and contraction of the engagement member 13 as each thread 82 of the plunger passes therethrough. In this mode, the engagement member 13 acts like a ratchet with minimal resistance as the plunger is advanced in the distal direction. In the preferred embodiment with a trailing flank angle of about 0 degrees, once a thread 82 has advanced through the engagement member in the distal direction the thread is prevented from moving backward in the proximal direction through the engagement member without rotating the plunger in the counterclockwise direction, i.e. unscrewing the plunger. In the preferred embodiment, inner surface 54 of throughbore 50 surrounds plunger 14 and is preferably in full contact with plunger 14 as the plunger moves therethrough. Preferably, there is an audible click coincident with each complete thread 82 passing the engagement member. By adjusting the pitch of the thread 82 relative to the cross-sectional area of barrel 12, this click represents a discrete volume of material ejected from the syringe. In a preferred embodiment, with a diameter of 0.625 inches and a thread pitch of 0.10 inches, one click represents 0.5 cc of material ejected from the syringe. This provides a user with a method of determining volume delivered.

The material can be expelled under high pressure by rotating head 80 of plunger 14 relative to barrel 12 in a clockwise direction. When the head is rotated, the distal end 74 of plunger 14 is progressively advanced into the central bore 16 of barrel 12. Threaded throughbore 70 and threaded stem 76 cooperate to translate external rotational forces applied to head 80 into longitudinal forces applied through the distal end 74 of plunger 16 to the bone cement material contained in barrel 12. It will be appreciated by those skilled in the art that the use of the threaded plunger makes it easier for the user to generate the forces needed within barrel 12 to extrude the material out of the distal end 22 of barrel 12 under relatively high pressures. It is noted that the shape of head 80 also allows the user efficiently to rotate plunger 16 with a minimal amount of hand and wrist rotation. The enlarged head 80 is shaped to facilitate ease of gripping and manipulation by the user. Those skilled in the art will appreciate that significant pressures can be generated within barrel 12 as plunger 16 is advanced into barrel 12 by rotating plunger 16 relative to barrel 12, particularly when highly viscous or solid, yet pliable bone cement compositions are situated within barrel 12. In that regard, in a preferred embodiment the mechanical advantage provided through the use of the threaded plunger is preferably about 5 to 1. In addition, the number of rotations (or fraction thereof) of plunger 14 relative to barrel 12 provides a means for metering the amount of material discharged from the distal end 22 of syringe 10. In one preferred embodiment incorporating the 0.10 inch pitch threads, each complete revolution (e.g., 360 degrees) of head 80 causes plunger 14 to advance longitudinally a sufficient distance to force 0.5 cc of material out the distal end 22 of barrel 12.

Figure 11B:
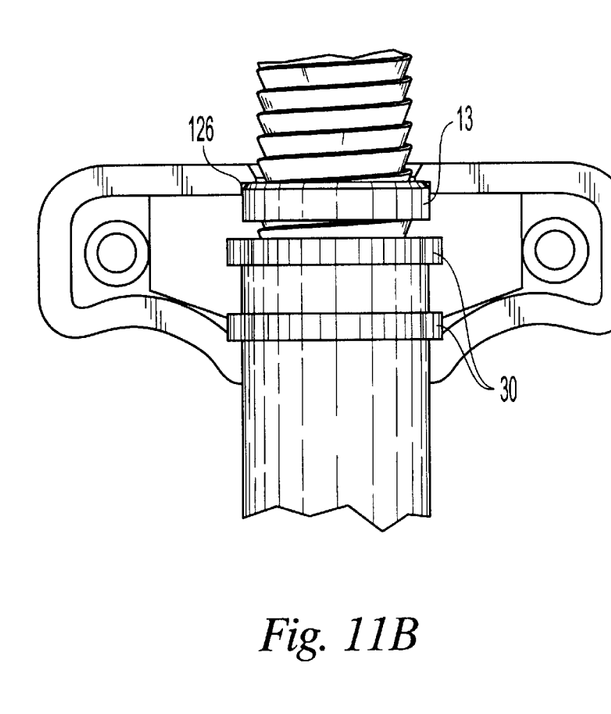

Referring to FIG. 11B, in one preferred embodiment, once the plunger is rotated in a clockwise direction, engagement member 13 is urged in the proximal direction and engages a seat portion 126 at the proximal interior of finger grip 34. Seat portion 126 preferably surrounds or traps at least a portion of the exterior of engagement member 13 and prevents the engagement member from expanding in the radial direction. This advantageously provides a rigid support for the engagement member so that the engagement member performs like a threaded nut and transfers the rotary motion of plunger 14 into an axial motion.

One of ordinary skill in the art can envision numerous variations and modifications to the invention disclosed herein. All of these modifications are contemplated by the true spirit and scope of the following claims.

What is claimed:

1. A syringe for delivery of a bone substitute material, comprising:
    a barrel for holding the material and having a longitudinal axis extending therethrough;
    a plunger receivable within the barrel and having a threaded portion; and
    an engagement member positioned coaxial with the barrel, the engagement member including a threaded throughbore having threads that are complimentary to the threaded portion of the plunger, the engagement member movable between a first position and a second position, wherein in the first position the plunger may advance through the engagement member by pushing the plunger in an axial direction, and in the second position the plunger may only advance through the engagement member by rotating the plunger.

2. The syringe of claim 1, wherein the cross-sectional area of the throughbore is variable.

3. The syringe of claim 1, wherein the throughbore includes an inner surface that is in full contact with the plunger when the plunger moves therethrough.

4. The syringe of claim 1, wherein the material exits the barrel under a first pressure when the plunger is pushed in the distal direction and the material exits the barrel under a second pressure when the plunger is advanced through rotation.

5. The syringe of claim 1, wherein a predetermined amount of expelled from the barrel when the barrel is advanced with each rotation of the plunger.

6. The syringe of claim 1, wherein the throughbore defines an inner surface and the inner surface is substantially threaded.

7. The syringe of claim 1, wherein the syringe further includes a needle attachment portion having at least one fin.

8. The syringe of claim 1, wherein the engagement member has a C-shape and includes a slot extending radially therethrough.

9. The syringe of claim 8, wherein the engagement member is expandable in the radial direction.

10. The syringe of claim 1, wherein an audible noise is as the threaded portion of the plunger moves past the engagement member when the plunger is pushed in the axial direction.

11. The syringe of claim 10, wherein a predetermined amount of material is expelled from the barrel with each audible noise.

12. The syringe of claim 1, further comprising a coupling member configured to receive a portion of a package containing material to facilitate the transfer of material from the package to the barrel.

13. The syringe of claim 12, wherein the coupling member includes a further to funnel the material into the barrel.

14. The syringe of claim 1, wherein the threaded stem includes at least one thread having a leading flank surface with a leading flank angle and a trailing flank surface with a trailing flank angle, the leading flank angle and the trailing flank angle being unequal.

15. The syringe of claim 14, wherein the leading flank angle is between about 45 to about 75 degrees and the trailing flank angle is between about 0 to about 10 degrees.

16. The syringe of claim 14, wherein the leading flank angle is about 60 degrees and the trailing flank angle is about 0 degrees.

17. The syringe of claim 1, wherein the barrel further includes a central bore having a cross-sectional area extending axial with the longitudinal axis, the central bore includes an inner surface that is in full contact with the plunger when the plunger moves therethrough.

18. The syringe of claim 17, wherein the central bore has a cross-sectional area that is variable.

19. The syringe of claim 17, wherein the syringe further includes an exit channel in fluid communication with the barrel, the exit channel having a cross sectional area the cross-sectional area of the barrel.

20. The syringe of claim 1, further comprising a finger grip coupled to the barrel at the proximal end, the engagement member housed within the finger grip.

21. The syringe of claim 20, wherein the finger grip comprises a pair of half shells.

22. The syringe of claim 20, wherein the engagement member is movable within the finger grip between the first position.

23. The syringe of claim 22, wherein the finger grip defines an inner wall and the engagement member includes an extension arm that contacts the inner wall of the finger grip when the engagement member is in the first position.

24. The syringe of claim 22, wherein the engagement member engages a seat for preventing the engagement member from expanding when the engagement member is in the second position.

25. The syringe of claim 1, wherein barrel has an interior wall, the interior a tapered portion at a distal barrel.

26. The syringe of claim 25, wherein the plunger includes an unthreaded distal tip with an annular recess located proximal thereof for receiving an O-ring sized and configured to provide a more effective seal against an inner surface of the barrel.

27. The syringe of claim 25, wherein the unthreaded tip has an angled tip angle tip surface having an angle greater than the angle of the tapered portion.

28. The syringe of claim 25, wherein the tapered portion has an angle of about 90 degrees and the angled tip surface has an angle of between about 95 and 145 degrees.

29. A syringe comprising:
- a barrel for holding the material and having a longitudinal axis extending the
- a plunger receivable within the barrel and having a threaded portion; and
- an engagement member positioned coaxial with the barrel, the engagement member including a threaded throughbore having threads that are complimentary to the threaded portion of the plunger to permit the plunger to be rotatable with respect to the engagement member;
- wherein the engagement member has a C-shape with a slot extending radially from the throughbore to an exterior surface of the engagement member to permit the engagement ember to expand in the radial direction so that the threaded portion can be axially movable through the threaded throughbore.

30. The syringe of claim 29, wherein the material exits the barrel under a first pressure when the plunger is pushed and the material exits the barrel under a second pressure when the plunger is rotatable.

31. The syringe of claim 29, wherein the engagement member is movable between a first position and a second position, wherein in the first position the plunger may advance through the engagement member by pushing the plunger in the axial direction, and in the second position the plunger may only advance through the engagement member by rotating the plunger.

32. The syringe of claim 29, wherein a predetermined amount of material is expelled from the barrel when the is advanced with each rotation of the plunger.

33. The syringe of claim 29, wherein the syringe further includes a needle attachment portion having at least one fin.

34. The syringe of claim 29, wherein an audible noise is made as the threaded portion of the plunger moves past the engagement member when the plunger is pushed the axial direction.

35. The syringe of claim 34, wherein a predetermined amount of material expelled from the barrel with each audible noise.

36. The syringe of claim 29, further comprising a coupling member configured to receive a portion of a package containing material to facilitate the transfer of material from the package to the barrel.

37. The syringe of claim 36, wherein the coupling member includes a funnel member to funnel the material into the barrel.

38. The syringe of claim 29, wherein the barrel further includes a central bore having a cross-sectional area extending axial with the longitudinal axis, the central bore includes an inner surface that is in full contact with the plunger when the plunger moves therethrough.

39. The syringe of claim 38, the central bore has a cross-sectional area that is variable.

40. The syringe of claim 38, wherein the syringe further includes an exit channel in fluid communication with the barrel, the exit channel having a cross sectional area smaller than the cross-sectional area of the barrel.

41. The syringe of claim 29, wherein at least one thread of the threaded flank surface with a leading flank angle and a trailing flank surface with a ank angle, the leading flank angle and the trailing flank angle being unequal.

42. The syringe of claim 41, wherein the leading flank angle is between about 45 to about 75 degrees and the trailing flank angle is between about 0 to about 10.

43. The syringe of claim 41, wherein the leading flank angle is about 60 degrees and the trailing flank angle is about 0 degrees.

44. The syringe of claim 29, further comprising a finger grip coupled to the barrel the proximal end, the engagement member housed within the finger grip.

45. The syringe of claim 44, wherein the finger grip comprises a pair of half shells.

46. The syringe of claim 44, wherein the engagement member is movable within the finger grip between a first position where the plunger is advancable by pushing the plunger in the axial direction and a second position where the plunger is advancable by rotating the plunger.

47. The syringe of claim 46, wherein the finger grip defines an inner wall and the engagement member includes an extension arm that contacts the inner wall of the finger grip hen the engagement member is in the first position.

48. The syringe of claim 46, wherein the engagement member engages a seat for preventing the engagement member from expanding when the engagement member is in the second position.

49. The syringe of claim 29, wherein barrel has an interior wall, the interior wall includes a tapered portion at a is end of the barrel.

50. The syringe of claim 49, the plunger includes an unthreaded distal tip with an annular recess located proximal thereof for receiving an O-ring sized and configured to provide a more effective seal against an inner surface of the barrel.

51. The syringe of claim 49, wherein the unthreaded tip has an angled tip surface, the angle tip surface having an greater than the angle of the tapered portion.

52. The syringe of clam 51, wherein the tapered portion has an angle of about 90 degrees and the angled tip surface has an angle of between about 95 and 145 degrees.

53. A syringe for delivery of a bone substitute material, comprising:
- a barrel for holding the material and having a longitudinal axis extending therethrough;
- a plunger receivable within the barrel and having a threaded portion; and
- a C-shape engagement member positioned coaxial with the barrel, the engagement member including a threaded throughbore having threads that are complimentary to the threaded portion of the plunger and a slot extending radially from the throughbore to an exterior surface of the engagement member;
- wherein the engagement member is movable between a first position and a second position, wherein in the first position the engagement member is radially expandable and the plunger is axially moveable through the engagement member and in the second position the engagement member is radially fixed and the plunger is rotatable with respect to the engagement member.

* * * * *